United States Patent [19]

Newhouse et al.

[11] Patent Number: 5,107,908

[45] Date of Patent: Apr. 28, 1992

[54] APPARATUS FOR SUPPORTING A CONTAINER FOR FLUID MATERIAL

[75] Inventors: Daniel L. Newhouse, Harrisburg; Leemer Cernohlavek, Fulton; Philip D. Lochhaas, Ashland, all of Mo.

[73] Assignee: Analytical Bio-Chemistry Laboratories, Inc., Columbia, Mo.

[21] Appl. No.: 728,728

[22] Filed: Jul. 11, 1991

Related U.S. Application Data

[62] Division of Ser. No. 347,519, May 3, 1989.

[51] Int. Cl.⁵ ............. B65B 43/42; B01D 15/08; G01N 35/06
[52] U.S. Cl. ........................... 141/130; 141/165; 141/372; 210/198.2; 210/635; 210/656
[58] Field of Search ............ 210/198.2, 635, 656; 73/61.1 C, 864.21, 864.23, 864.22, 864.24, 864.25; 436/47; 141/130, 372, 165, 172; 222/400.7, 400.8

[56] References Cited

U.S. PATENT DOCUMENTS

| | | | |
|---|---|---|---|
| 532,235 | 1/1995 | Grap | 141/372 |
| 713,160 | 11/1902 | Schneider | 141/372 |
| 732,123 | 6/1903 | Schneider | 141/372 |
| 1,521,928 | 1/1925 | Campbell | 141/372 |
| 2,846,121 | 8/1958 | Ronnebeck | 73/23.42 |
| 3,534,788 | 10/1970 | Vergobbi et al. | 141/372 |
| 3,677,091 | 7/1972 | Guigan | 73/864.22 |
| 3,744,219 | 7/1973 | Tindle et al. | 55/162 |
| 3,912,456 | 10/1975 | Young | 73/864.22 |
| 3,925,207 | 12/1977 | Scriba | 210/198.2 |
| 4,042,499 | 8/1977 | Ramstad et al. | 210/198.2 |
| 4,108,602 | 8/1978 | Hanson et al. | 73/864.22 |
| 4,217,223 | 8/1980 | Baba et al. | 210/198.2 |
| 4,478,095 | 10/1984 | Bradley et al. | 422/64 |
| 4,604,363 | 8/1986 | Newhouse et al. | 159/47.1 |
| 4,609,017 | 9/1986 | Coulter et al. | 141/130 |
| 4,662,411 | 5/1987 | Zimmerman et al. | 141/130 |
| 4,674,323 | 6/1987 | Rulf et al. | 364/497 |
| 4,721,138 | 1/1988 | Simonazzi | 141/372 |
| 4,865,090 | 9/1989 | Burolla et al. | 141/372 |
| 4,951,512 | 8/1990 | Mazza et al. | 141/130 |
| 5,012,845 | 5/1991 | Averette | 141/130 |

Primary Examiner—Stanley S. Silverman
Assistant Examiner—Cynthia L. Nessler
Attorney, Agent, or Firm—Epstein, Edell & Retzer

[57] ABSTRACT

Automated gel permeation chromatography of multiple individual samples is effected with high precision and high speed utilizing a common sample sizing loop into which each sample is placed prior to its injection into the chromatography column, thereby eliminating the need for precisely matched sample loops. Each sample is pre-stored in its own container, the containers being automatically sequentially accessed to feed a portion of the contained sample medium to the common sample sizing loop. The common sample flow path, including the sample sizing loop, is automatically cleaned with rinse solvent between loading of successive samples into the sizing loop. Multiple programs may be employed to control the processing times for different types of sample fluid. A sample container closure member having a unique sealing insert member is provided to preclude leakage of fluid from the sample storage container when the container is pressurized.

14 Claims, 3 Drawing Sheets

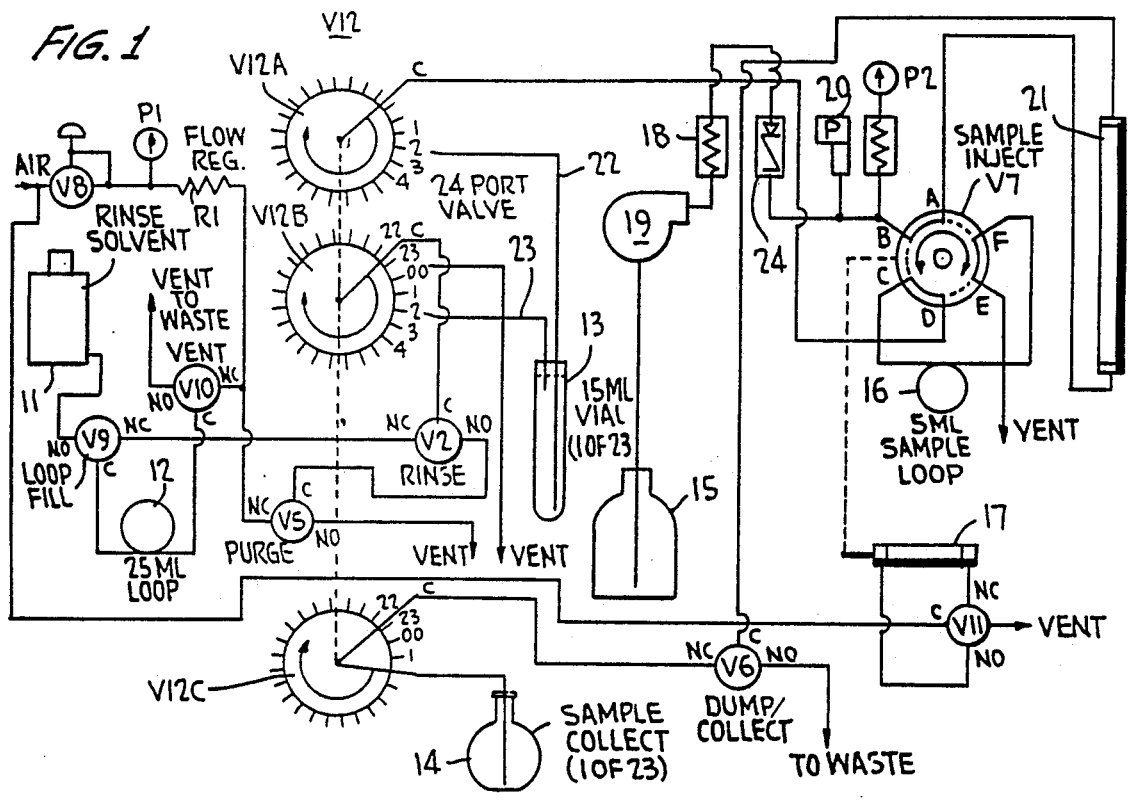

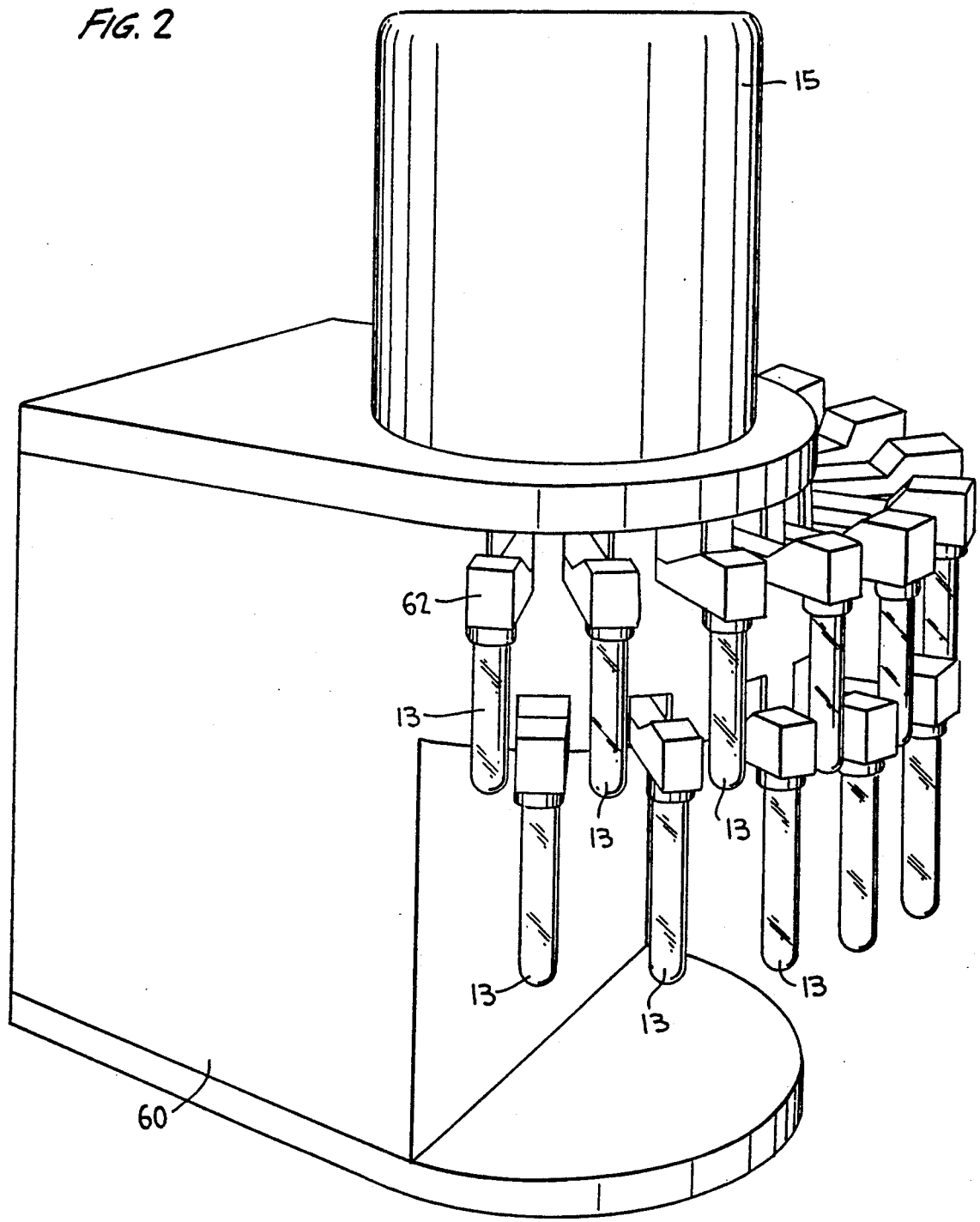

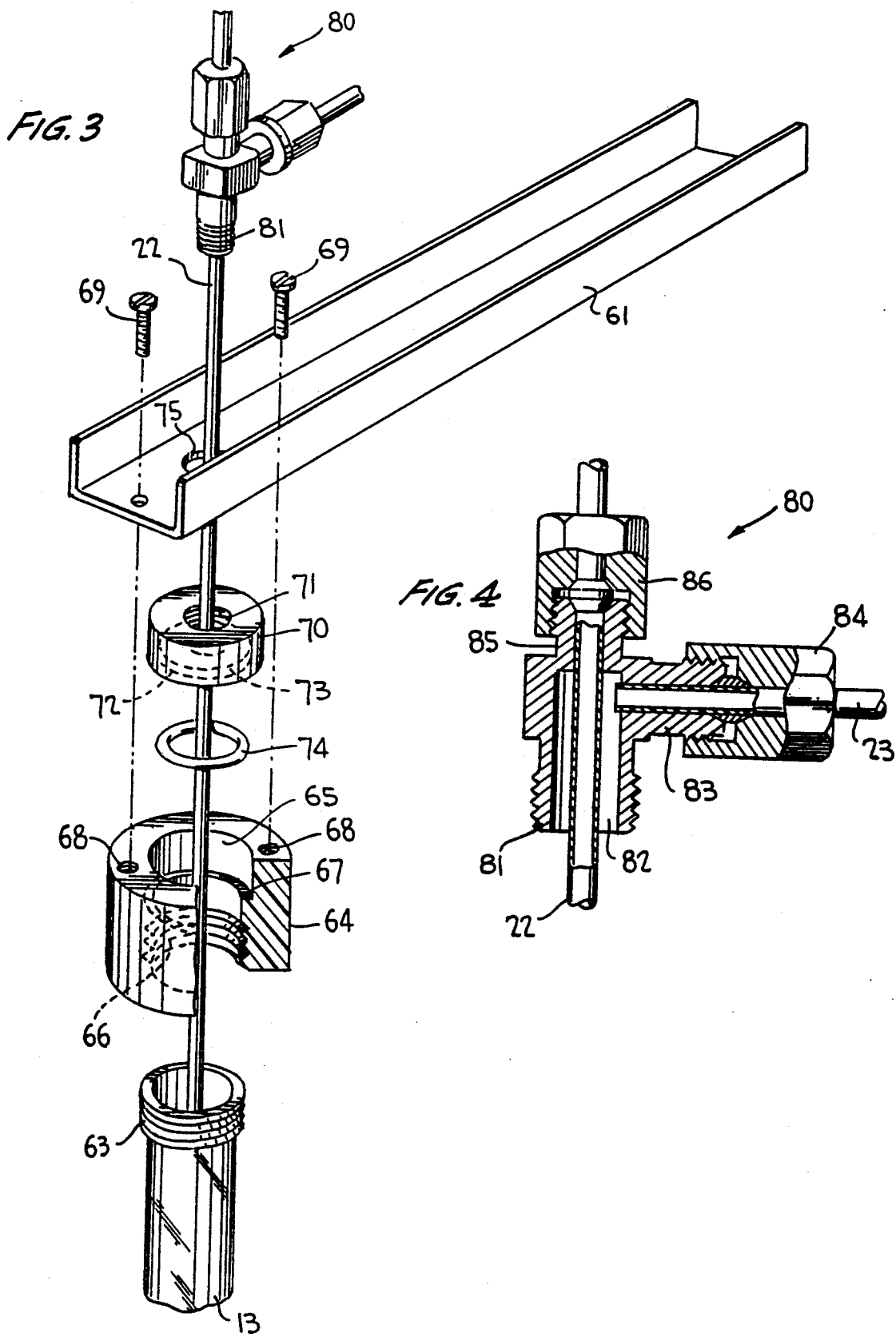

APPARATUS FOR SUPPORTING A CONTAINER FOR FLUID MATERIAL

This is a divisional application of application Ser. No. 07/347,519, filed May 3, 1989.

BACKGROUND OF THE INVENTION

1. Technical Field:

The present invention relates to improvements in automated chromatography systems.

2. Discussion of the Prior Art:

Gel permeation chromatography is a well known technique for separating and retaining selected residue components from lipids, sludges, soil, etc. An automated liquid chromatography system employing gel permeation is disclosed in U.S. Pat. No. 3,744,219 (Tindle et al). In the Tindle et al system up to twenty-three individual sample loops or containers are filled with crude sample media, and each sample is sequentially injected into a gel permeation column. As an injected sample is forced through the column, the larger molecules, which are usually the unwanted components of the sample, exit from the column first and are discarded. The smaller molecules to be eluted travel through the gel pores and thereby follow a relatively long and tortuous path to exit from the column after the unwanted larger molecules which are excluded from the pores and therefore travel a more direct path through the column.

Although the Tindle et al automated system represents a significant improvement over prior manually-operated systems, it nevertheless has certain inherent disadvantages and drawbacks. For example, each sample must be loaded into a separate respective sample sizing loop. Since subsequent analysis and processing are greatly simplified if all samples have the same volume, the twenty-three loops must have volumes that are precisely matched within one percent. In addition, the process of loading samples into the respective sample loops is relatively time-consuming, particularly in the case of viscous sample fluids. Further some samples, while awaiting processing, tend to crystallize or otherwise fall out of solution in their respective loops, resulting in flow restrictions in the system flow path and/or loss of sample material. Moreover, after each loop has been filled with sample fluid by a common syringe, the flow paths, leading to the remaining loops, including the loading syringe, must be manually cleansed, thereby increasing the total time required for sample loading.

Another limitation of the Tindle et al system resides in the fact that once the system is placed in the automatic operation mode, no further samples may be added for processing. All of the samples to be processed must be loaded in sequence, starting with the first sample loop, prior to the initiation of automatic processing. Moreover, all samples must be similar in composition.

In systems of the type described herein, wherein sample fluid is transported between different locations by purge gas or other pressurized fluid, there is a tendency for sample storage containers to leak under the relatively high pressure of the purge gas. Apart from aesthetic considerations, the loss of sample fluid by leakage can result in inaccurate processing by causing variations from the standard volume in any given sample.

OBJECTS AND SUMMARY OF THE INVENTION

It is therefore an object of the present invention to provide a method and apparatus for performing automated gel permeation chromatography wherein the aforementioned drawbacks and disadvantages are substantially eliminated.

In accordance with the present invention a single or common sample sizing container or loop is provided. Each sample is placed in the common sample loop immediately prior to injection of that sample into the chromatography column, thereby eliminating the requirement for multiple precisely matched sample loops. Since a common sample loop is used to size each sample, the volume is identical for each sample injected into the chromatography column. Before sizing, each sample is stored in its own storage flask, the flasks being automatically sequentially accessed to directly feed a portion of the contained sample medium to the common sample sizing loop. Accordingly, the present invention eliminates the need for a common loading flask that must be carefully cleaned between sample loadings in the Tindle et al system. The overall result is a greatly reduced total sample loading time. The present invention is specifically directed to a sample storage flask suspended from a respective support arm extending outwardly from the chromatographic unit housing. A container closure member is secured flush against the underside of the support arm and has a vertical bore defined entirely through its axial length. The bottom portion of the insert bore is of smaller diameter and is threaded to receive the upper end of its storage flask in a threaded fit engagement. The upper end of the insert bore is of shorter length and larger diameter, thereby defining an upwardly facing annular shoulder at the juncture of the two bore sections. A closure insert fits flush within the upper bore section and has an axially-extending bore defined therein in concentric alignment with the closure member bore. The bottom section of the insert bore is relatively short and has a slightly larger diameter than the diameter of the upper bore section in the closure member. An O-ring is disposed in the bottom section of the insert bore and is urged against the annular shoulder in the closure member bore when the insert member is properly seated in the closure member. The upper insert bore section is threaded to receive a threaded bottom leg of a hollow connector disposed above the support arm in registration with an access hole defined in the support arm and aligned with the insert and closure member bores. A sample pickup tube extends through the connector, the access hole and the concentric bores in the insert and closure members into the flask. A second tube for selectively delivering solvent and purge gas to the flask terminates at the connector so as to deliver its fluid to the hollow connector interior. The delivered fluid flows in an annular path surrounding the pick-up tube into the flask via the concentric bores in the insert and closure members. The closure member is secured against the underside of the support arm by means of screws so as to tightly engage the insert member in its seated position in the closure member bore.

BRIEF DESCRIPTION OF THE DRAWINGS

These and other objects, features and many of the attendant advantages of the present invention will be appreciated more readily as they become better understood from a reading of the following description considered in connection with the accompanying drawings wherein like parts in each of the several figures are identified by the same reference characters, and wherein:

FIG. 1 is a flow schematic diagram of a preferred embodiment of the chromatography system of the present invention;

FIG. 2 is a view in perspective of the chromatography module housing of the system of FIG. 1;

FIG. 3 is an exploded view in perspective of a typical support arm extending from the housing of FIG. 2, and FIG. 4 is a view in vertical section of a connector employed in the support arm assembly of FIG. 3.

DESCRIPTION OF THE PREFERRED EMBODIMENT

Reference is initially made to FIG. 1 of the accompanying drawings which is a flow diagram of a preferred embodiment of the chromatography system of the present invention. A chromatography column 21 is utilized to separate components from sample fluids passed therethrough in a conventional manner. In the preferred embodiment, column 21 is typically made of glass with teflon fittings and packed with spherical beads of styrene divinyl benzene three percent cross-linked polymer. Smaller molecules enter and exit from the gel pores following a longer path through the column and elute later than larger molecules that are excluded from the pores and travel a more direct path to the top of the column. The bottom of input end of the column 21 is connected by a fluid conduit to a port A of the sample inject valve V7 which is a six-port, two-position valve such as the type disclosed in U.S. Pat. No. 2,846,121. In one position of valve V7 (i.e., the load position shown in solid lines), ports A and B are in flow communication, ports C and D are in flow communication and ports E and F are in flow communication. When valve V7 is in the run position, ports A and F are in flow communication, ports D and E are in flow communication and ports B and C are in flow communication. Port E is permanently connected to a vent or waste container. Operation of the sample inject valve V7 is controlled by an air cylinder 17, the piston in which is moved under the control of a piston control valve V11. Valve V11 has a common port C, a normally closed port NC, a normally open port NO and a vented port. When valve V11 is unactuated, the normally closed port is in flow communication with the vented port while the common port is in flow communication with the normally open port. Upon actuation of valve V11, its common port is in flow communication with the normally closed port while the normally open port is in flow communication with the vent port.

A common sample sizing loop 16 is connected between ports C and F of the sample inject valve V7. In the preferred embodiment sample loop 16 has a five milliliter volume, although this is not a limiting characteristic of the present invention. The volume of sample loop 16 must be sufficient to permit the sample contained therein to be properly processed through column 21. Sample loop 16 serves as a common sizing container for sample material to be analyzed and, in this regard, may take the form of any suitable container. It should be noted, however, that a loop of fluid-conducting tubing is particularly useful as a sizing container in the present invention.

Multiple sample storage containers 13 (only one of which is illustrated in FIG. 1 to facilitate understanding of the invention) take the form of respective test tubes or flasks in which sample material to be analyzed is stored. The outer surface of each container 13 is threaded at its upper end to be engaged by a suitable respective threaded closure member. A respective sample pick-up tube 22 extends from the bottom of each container 13 to a respective individually accessible port of a first wafer or section V12A of a multiple port sample selection valve V12. The length to which the pick-up tube 22 extends in container 13 may be adjustable. Valve V12 has three simultaneously actuable and substantially identical sections V12A, V12B and V12C, each section having a common port C that is selectively placed in flow communication with twenty-four individually accessible ports numbered "00" through "23". The twenty-four individually accessible ports at each section correspond to one more than the number of sample storage containers 13 with the "00" port serving as a neutral position for valve V12. In the flow diagram of FIG. 1 the single sample storage container 13 is shown with its pick-up tube 22 connected to individually accessible port "2" of valve section V12A. The common port of valve section V12A is connected to port D of sample inject valve V7 so that sample fluid from the sample storage container 13 selected by valve V12 can pass through the common port of valve section V12A to port D of the sample inject valve where, in the load position of valve V7, the sample passes from port C of the valve into the sample loop 16.

Each sample storage container 13 is provided with a fluid delivery tube 23 extending from the upper portion of the container to a corresponding individually accessible port of valve section V12B. In particular, the individually accessible port at V12B to which delivery tube 23 is connected corresponds to the individually accessible port in valve section V12A to which the pick-up tube 22 for the corresponding sample storage container 13 is connected. The common port C for valve section V12B is connected to receive either purge gas or rinse liquid in a manner described below.

From the foregoing it will be seen that valve sections V12A and V12B are used to provide sample selection. Valve section 12A connects each of the twenty-three sample pick-up tubes 22 to either the sample loop 16 or to vent, depending upon the position of sample inject valve V7. Valve section V12B connects each of the twenty-three delivery tubes 23 to the supply line for purge gas or rinse liquid. The "00" port of valve section V12B is connected to vent.

The third valve section V12C has its individually accessible ports connected to respective sample collection containers 14, there being twenty-three such sample collection containers but only one is illustrated in FIG. 1 to facilitate understanding of the system. The common port C for valve section V12C is connected to a normally closed port of a dump/collect valve V6. Valve V6 also has a common port which is connected to the normally closed port when the valve is actuated, and a normally open port to which the common port is connected when the valve is unactuated. The normally open port of valve V6 is connected to waste or vent. The common port of valve V6 is connected to the upper end of the chromatography column 21. It will be appreciated, therefore, that valve section V12C connects each of the twenty-three sample collection containers 14 to the dump/collect valve V6 in order to permit the eluted component of the processed sample to be collected from column 21. As each sample is selected for processing, valve V12 is stepped by means of a solenoid in all three valve sections simultaneously. Sample position feedback is provided to the controller unit in a manner described below.

A reservoir 15 for sample solvent material has solvent material selectively drawn therefrom by means of a solvent pump 19 that is selectively actuable. Solvent pump 19 is a positive displacement piston pump having an adjustable flow rate. Typically the sample solvent reservoir 15 has an eight liter capacity. The sample solvent fluid is used to drive the sized sample in sample loop 16 through the chromatography column 21. In this regard, the outflow from sample solvent pump 19 is directed to port B of the sample inject valve V7. The flow path between pump 19 and port B of valve V7 includes a snubber 18, and a check valve 24. A pressure gauge P2 measures the pressure at the outflow side of check valve 24, and an over-pressure switch 20 monitors the pressure at the same location. If the monitored pressure exceeds a predetermined maximum (e.g., 20 psi), over-pressure switch 20 is actuated to provide a signal to the system controller which responds by terminating processing and shutting off the solvent pump 19. Snubber 18 serves to protect the presssure gauge P2 and prevent fluctuations of the guage indicator.

The common port C for sample select valve section V12B is connected to the common port C of rinse valve V2. Rinse valve V2 is the same type of valve described above in relation to valve V6 and has its normally open port connected to the common port of a purge valve V5 also of the same general type. The normally closed port of rinse valve V2 is connected to the normally closed port of a loop fill valve V9, also of the same general type. Purge valve V5 has its normally open port vented while its normally closed port is connected to receive a supply of purge gas under pressure. The purge gas is supplied through a pressure and flow regulation path including a pressure regulator valve V8 and a flow restrictor R1. A pressure gauge P1 monitors the pressure of the purge gas downstream of pressure regulator valve V8. The normally closed port of vent valve V10 is also connected to receive the regulated pressurized purge gas, the normally open port of that valve being vented.

A rinse solvent reservoir 11 is connected so that outflow therefrom is delivered to the normally open port of loop fill valve V9. The common port of loop fill valve V9 is connected to one side of a rinse loop 12 which, in the preferred embodiment, is a length of tubing having a volume of 25 milliliters. When it is desired to deliver rinse solvent from loop 12 to the common flow path, valves V2, V9 and V10 are actuated, thereby permitting the pressurized purge gas to force the rinse solvent from the rinse loop 12. When these valves are unactuated, the rinse loop is gravity filled with rinse solvent from reservoir 11.

Operation of the flow components illustrated in FIG. 1 proceeds in timed relation under the control of the programmed system microprocessor described in the above cross-referenced and co-pending U.S. patent application Ser. No. 07/347,519. For a broad overview of system operation, the following description is presented.

Solvent pump 18 is actuated prior to sample processing until the solvent pressure and flow rate, as measured at the output of check valve 24, stabilize at the desired levels. During this time sample solvent is pumped from solvent reservoir 15 through snubber 18, check valve 24 and sample inject valve V7 (port B), out through port A of valve V7 and through the column 21 to a waste container via valve V6. The pressure of the solvent is indicated by pressure gauge P2. If the system pressure exceeds a predetermined maximum (e.g., 20 psi) at any time during solvent pump operation, the over pressure switch 20 generates a signal to the system controller which halts operation by de-energizing pump 19 and displaying an error indication for the operator.

Sample processing is initiated by actuation of the "run" key (described below). The sample select valve V12 is actuated to the position corresponding to the first sample to be processed as pre-programmed by the operator. Gas purge valve V5 is energized to allow the purge gas to flow through unactuated rinse valve V2 and into the selected sample container 13 via the appropriate individually accessible port in section V12B of the sample select valve. The purge gas enters the top of the sample container 13 via delivery tube 23 and forces sample fluid out of the container via pick-up tube 22. The sample fluid flows through valve section V12A and ports D and C of sample inject valve V7 into the common sample sizing loop 16. Purge gas flow rate and sample load time are calibrated prior to sample processing to assure that a small portion of the sample flows through the sample loop to vent, leaving the sample loop completely filled with sample fluid. A small amount of sample fluid is also left in the tube connecting the common port of valve section V12A with port D of the sample inject valve V7. This tube is maintained as short as possible in order to minimize the amount of sample fluid retained therein since that retained fluid is ultimately discarded.

At the end of the sample load time the piston control valve V11 is energized to actuate air piston 17, thereby switching the sample inject valve V7 from its load position (i.e., solid lines in FIG. 1) to its run position (i.e., dashed lines in FIG. 1). The programmable dump interval is initiated at this time. Purge valve V5 remains actuated briefly after the dump interval commences in order to drive out to vent any sample fluid remaining in container 13 and pick-up tube 22, and in the tubing between the common port of valve section V12A and port D of valve V7. Solvent fluid is pumped from the sample solvent reservoir 15, through the sample inject valve V7 to ports D and C, through sample loop 16 and into the bottom of column 21. The sample solvent from reservoir 15 thus drives the sample fluid previously loaded into the common sample loop 16 through column 21. The dump/collect valve V6 is not actuated at this time so that the initial column effluent (i.e., from the top of the column) is directed to a waste container.

The initiation of the dump interval also results in rinse solvent fluid from rinse loop 12 being driven through the path taken by the previously loaded sample. In particular, loop fill valve, V9, vent valve V10 and rinse valve V2 are energized, thereby permitting purge gas to force rinse solvent from loop 12, through valves V10 and V2 and valve section V12B into the selected sample container 13. The rinse solvent rinses container 13 and is forced through pick-up tube 22, valve section V12A, and ports D and E of the sample inject valve V7 to waste. This results in a rinsing or cleansing of the common line between section V12A of the sample select valve and port D of sample inject valve V7 through which the next selected sample must pass when loaded into the common sample sizing loop 16.

After an appropriate time interval to effect cleansing, vent valve V10 and rinse valve V2 are de-energized, while loop fill valve V9 is permitted to remain energized briefly to aid in refilling the gravity-filled rinse loop 12. Purge valve V5 is energized to force the remainder of the rinse solvent fluid out to the waste container at port E of sample inject valve V7. Rinsing thus takes place during the dump interval resulting in a minimization of the dump interval (i.e., typically on the order of ninety seconds). At the end of the rinsing portion of the interval, purge valve V5 is de-energized. Rinsing can also be initiated during various servicing and maintenance prompts by actuating an appropriate rinse purge switch described subsequently.

At the end of the dump interval, dump/collect valve V6 is energized to permit the effluent from column 21 to be directed through section V12C of the sample select valve and into the appropriate sample collection container 14. At the termination of the prescribed collection interval, dump/collect valve V6 is de-energized so that the column effluent may be directed to a waste container for the duration of the wash interval. At the termination of the wash interval, or at the termination of the collect interval if the wash interval is selected to be zero, processing continues with the next sample in the manner described above. If no further samples are to be processed, the solvent pump 19 is de-energized and processing is terminated.

Operation of the flow components during the sytem calibration mode is identical to normal run operation described above until the end of the collect interval. Instead of proceeding to a wash interval, the collect interval is reset to the programmed value, the sample select valve V12 is stepped to the next position, the dump/collect valve V6 remains energized, and sample collection continues with the next sample in sequence. The process continues in the manner described until all samples are collected and processed.

Referring now to FIGS. 2, 3 and 4, A chromatography unit includes a housing 60 at the top of which is located the sample solvent reservoir 15. Each of the sample storage containers 13 is suspended outwardly from housing 60 by a respective support arm 61 having a cover 62. It will be noted that covers 62 preclude viewing the support arms 61 in FIG. 2, and that the cover 62 is removed from the single support arm illustrated in FIG. 3. Each sample storage container 13 has its upper end externally threaded at 63 to permit it to be engaged by a closure member 64. Closure member 64 preferably has a cylindrical configuration and is made of a suitable plastic material. A closure member bore extends axially between the top and bottom surfaces of the closure member and includes a top section 65 and a threaded bottom section 66. Top bore section 65 is diametrically enlarged relative to bottom bore section 66 which is threaded so as to engage the threaded top portion 63 of container 13. An annular shoulder 67 faces upwardly and demarks the transition between bore sections 65 and 66. Two tapped holes 68 are defined in the top surface of closure member 64 to permit the closure member to be secured to the underside of support arm 61 by means of screws 69 extending through suitably provided mounting holes in support arm 61. When thusly mounted, the top surface of the closure member 64 is flush against the underside of support arm 61.

A closure insert 70 has a generally cylindrical periphery sized to be snugly received in top bore section 65 in closure member 64. When thusly secured, the top surface of closure insert 70 is flush with the top surface of closure member 64. More specifically, the axial length of insert 70 is substantially equal to the axial length of top bore section 65. Closure insert 70 also has an axial bore defined therethrough. The closure insert bore includes an upper threaded portion 71 of relatively small diameter, and a shorter lower portion of somewhat larger diameter. The two bore portions 71 and 72 meet at a downwardly facing annular shoulder 73. An O-ring 74 is disposed in lower insert bore portion 72 and is contained between annular shoulders 73 and 67 when insert member 70 is fully inserted into the upper section 65 of the closure bore.

Support arm 61 has an access hole 75 defined therein in substantial axial alignment with the closure and insert bores, thereby permitting pick-up tube 22 to be extended through access hole 75, insert 71 and closure member 64 into the sample storage container 13. Pick-up tube 22, which extends from the sample storage container interior to a respective accessible port at section V12A of the twenty-four port valve, also extends through a connector 80. The connector includes a bottom male fitting 81 threaded to be engaged by the threaded upper portion 71 of the insert bore. In this regard, fitting 81 projects through access hole 75 in support arm 61 into the insert member 70 in fluid sealing relation. The fluid seal may be enhanced by wrapping suitable sealing tape about the threaded portion of fitting 81 before engaging the fitting in threaded bore section 71. The interior of connector 80 is hollow and diametrically larger than pick-up 22 so that an annular space 82 surrounds tube 22 and communicates with the top of container 13 via the bores in insert 70 and closure member 64.

Delivery tube 23, described above as alternatively supplying purge gas and rinse fluid to the sample storage containers 13, extends radially into annular space 82 through a side fitting 83 in which tube 23 is frictionally engaged. Side fitting 83 is externally threaded to be engaged in a locking sleeve 84 through which delivery tube 23 also extends. Sleeve 84 serves to engage fitting 83 in fluid sealing relation. A top fitting 85 of connector 80 receives pick-up tube 22 in frictional engagement and is externally threaded to be engaged by a locking sleeve 86 through which pick-up tube 22 also extends. Sleeve 86 engages top fitting 85 in fluid sealing relation.

It will be appreciated that delivery of purge gas into the annular space 82 in connector 80 via delivery tube 23 results in pressurization at the top of sample storage container 13. This pressurization by the purge gas is applied to the surface of the sample fluid in container 13 and forces fluid up through the pick-up tube to the appropriate accessible port at valve section V12A. The use of insert member 70 in connection with O-ring 74 at the upper end of the closure member bore has proven to be exceedingly effective in eliminating leakage of fluid under pressure from the juncture of the sample storage container 13 and closure member 64.

The support arm 61 is configured in the form of a channel adapted to receive the pick-up tube 22 and delivery tube 23 extending from connector 80 back into housing 60. Cover member 62 is configured to enclose both tubes 22 and 23 and connector 80 within the space defined by the channel-shaped support arm 61 and its cover 62.

From the foregoing description it will be appreciated that the present invention makes available a novel single-loop chromatography method and apparatus wherein a technique for automatically loading samples into a common sample sizing loop significantly reduces the time required for loading the system and initiating operation as compared to prior art systems. Operation of the system can be initiated immediately after the first sample is loaded into the sample sizing loop, while leakage and other hazards associated with syringe loading have been eliminated by the automatic loading approach. Plural operating programs are provided to permit processing of various sample types, and carry-over contamination from sample to sample is eliminated with an automatic rinsing process. The common sample sizing loop allows for greater precision and samples may be added to the system while another sample is being processed. A unique sealing arrangement is provided for each storage sample container suspended from a support arm so as to prevent leakage when the sample container is pressurized during loading and rinsing procedures.

Having described a preferred embodiment of a new and improved single-loop chromatography method and apparatus, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed:

1. Apparatus for supporting a container for fluid material comprising:
   the housing;
   a support arm having a proximal end secured to said housing and a distal end remote from said housing, said distal end having a top side and an underside;
   attachment means for suspending said container from the distal end of said support arm, said attachment means comprising:
      a closure member having top and bottom surfaces and an axially-extending closure bore defined therein between said top and bottom surfaces, wherein said closure bore includes a top section and a bottom section, said top section being diametrically enlarged relative to said bottom section to thereby define an upwardly-facing annular shoulder at the juncture between said top and bottom sections, and wherein said bottom section is sized to receive and engage an upper end of said container;
      a closure insert disposed in and radially dimensioned to correspond to the top section of the closure bore and having a top surface disposed substantially flush with the top surface of said closure member;
      wherein said closure insert has an axial insert bore defined therethrough in coaxial alignment with the closure bore;
      an O-ring disposed between said closure insert and said upwardly-facing shoulder;
      wherein said support arm has an access hole defined through from said top side to said underside;
      means securing said closure member to said support arm with the top surface of the closure member flush against said underside and with said access hole aligned with said insert and closure bores to permit conduction of fluid between said container and a location above the top side of said support arm;
      connector means disposed proximate the top side of said support arm and having a hollow body and a bottom male fitting
      a first tube extending through said hollow connector body, said bottom male fitting and the aligned insert and closure bores into said container, said tube and said hollow connector body defining an annular flow path therebetween; and
      fluid conduit means extending from said connector means in flow communication with the upper end of said container via said annular flow path and said insert and closure bores.

2. The apparatus according to claim 1 wherein said connector means includes a first top fitting disposed above said top side of said support arm, and wherein said first tube extends through said first top fitting into said hollow connector body.

3. The apparatus according to claim 1 wherein said connector means further includes a top fitting disposed above said top side of said support arm, and wherein said fluid conduit means is secured to said top fitting.

4. The apparatus according to claim 1 wherein said insert bore includes two axial portions, namely an upper portion of relatively small diameter and a lower portion of relatively large diameter, said upper and lower portions joining one another at a downwardly-facing annular shoulder; and
   wherein said O-ring is disposed in said lower portion of said insert bore and contained between said upwardly-facing shoulder and said downwardly-facing shoulder.

5. The apparatus according to claim 4 wherein said upper portion of said insert bore is threaded, and wherein said bottom male fitting is externally threaded to engage the upper threaded portion of said insert bore.

6. The apparatus according to claim 1 wherein said closure insert has an axial length substantially equal to the axial length of the top section of said closure bore.

7. The apparatus according to claim 6 wherein said insert bore includes two axial portions, namely an upper portion of relatively small diameter and a lower portion of relatively large diameter, said upper and lower portions joining one another at a downwardly-facing annular shoulder; and
   wherein said O-ring is disposed in said lower portion of said insert bore and contained between said upwardly-facing shoulder and said downwardly-facing shoulder.

8. The apparatus according to claim 7 wherein said upper portion of said insert bore is threaded, and wherein said bottom male fitting is externally threaded to engage the upper threaded portion of said insert bore.

9. The apparatus according to claim 8 wherein said first tube extends to approximately the bottom of said container.

10. The apparatus according to claim 8 adapted to further support multiple containers, said apparatus further comprising:
   a multiplicity of support arms, each for supporting a respective container, secured to said housing and configured substantially identically; and
   a multiplicity of said attachment means, each for suspending a respective container from a respective support arm and configured substantially identically.

11. The apparatus according to claim 8 wherein said connector means further includes a top fitting disposed above said top side of said support arm, and wherein said fluid conduit means is secured to said top fitting.

12. The apparatus according to claim 8 wherein said connector means includes a first top fitting disposed above said top side of said support arm, and wherein said first tube extends through said first top fitting into said hollow connector body.

13. The apparatus according to claim 12 wherein said connector means further includes a second top fitting disposed above said top side of said support arm, and wherein said fluid conduit means is secured to said second top fitting.

14. Apparatus for use in a chromatography system having multiple sample storage containers from which fluid material is sequentially withdrawn via a pick-up tube, said apparatus comprising:
   a system housing;
   multiple support arms each having a proximal end secured to said housing and a distal end remote from said housing, said distal end having a top side and an underside;
   multiple attachment means for suspending a respective sample storage container from the distal end of a respective support arm, each said attachment means comprising:
      a closure member having top and bottom surfaces and an axially-extending closure bore defined therein between said top and bottom surfaces, wherein said closure bore includes a top section and a bottom section, said top section being diametrically enlarged relative to said bottom section to thereby define an upwardly-facing annular shoulder at the juncture between said top and bottom sections, and wherein said bottom section is sized to receive and engage an upper end of a respective sample storage container;
      a closure insert having an axial length substantially equal to the axial length of the top section of said closure bore and radially dimensioned to correspond to the top section of the closure bore so that the closure insert fits snugly in the top section of the closure bore with the top of said closure insert substantially flush with the top surface of said closure member;
      wherein said closure insert has an axial insert bore defined therethrough in coaxial alignment with the closure bore, said insert bore having two axial portions, namely an upper threaded portion of relatively small diameter and a lower portion of relatively large diameter, the upper and lower portions joining one another at a downwardly-facing annular shoulder;
      an O-ring disposed in said lower portion of said insert bore and contained between said upwardly-facing shoulder and said downwardly-facing shoulder;
      wherein each support arm has an access hole defined through from said top side to said under side;
      means securing said closure member to said respective support arm with the top surface of said closure member flush against said underside and with said access hole aligned with said insert and closure bores to permit conduction of fluid between said respective sample storage container and a location above said top side of said respective support arm;
      connector means disposed proximate said top side of said respective support arm and having a hollow body, a bottom male fitting extending through said access hole and threaded to engage said upper threaded bore portion of said closure insert, and first and second top fittings;
      a first tube extending through said first top fitting, said hollow connector body, said bottom male fitting and the aligned insert and closure bores to approximately the bottom of said sample storage container;
      fluid conduit means secured to said second top fitting in flow communication with the upper end of said sample storage container via the hollow connector body and an annular flow path disposed about said first tube through said bottom fitting and said insert and closure bores.

* * * * *